(12) United States Patent
Bae et al.

(10) Patent No.: US 8,937,038 B2
(45) Date of Patent: Jan. 20, 2015

(54) COMPOSITION CONTAINING PEPTIDE LIGAND THAT BONDS WITH CXCR2 FOR TREATING INFECTIVE AND INFLAMMATORY DISEASES

(75) Inventors: Yoe Sik Bae, Seongnam-si (KR); Sang Doo Kim, Yangsan-si (KR)

(73) Assignee: Research & Business Foundation Sungkyunkwan University, Suwon-si (KR)

( * ) Notice: Subject to any disclaimer, the term of this patent is extended or adjusted under 35 U.S.C. 154(b) by 0 days.

(21) Appl. No.: 13/880,889

(22) PCT Filed: Oct. 19, 2011

(86) PCT No.: PCT/KR2011/007807
§ 371 (c)(1),
(2), (4) Date: Apr. 22, 2013

(87) PCT Pub. No.: WO2012/053827
PCT Pub. Date: Apr. 26, 2012

(65) Prior Publication Data
US 2013/0252878 A1    Sep. 26, 2013

(30) Foreign Application Priority Data
Oct. 22, 2010  (KR) ........................ 10-2010-0103259

(51) Int. Cl.
*C07K 5/097* (2006.01)
*A61K 38/06* (2006.01)

(52) U.S. Cl.
CPC .............. *C07K 5/0823* (2013.01); *A61K 38/06* (2013.01)
USPC ........................... 514/1.4; 514/18.9; 514/21.9

(58) Field of Classification Search
CPC .............................. A61K 38/06; C07K 5/0823
USPC ........................................ 514/18.9, 1.4, 21.9
See application file for complete search history.

(56) References Cited

U.S. PATENT DOCUMENTS

2002/0107202 A1  8/2002  Haddox et al.
2003/0077705 A1  4/2003  Gordon et al.
2004/0208873 A1  10/2004  Teeling et al.

FOREIGN PATENT DOCUMENTS

WO  WO 2005/103702 A2  11/2005

OTHER PUBLICATIONS

Weathington Nathanial, A novel peptide CXCR ligand derived from extracellular degradation during airway inflammation, Nature Medicine, Mar. 2006, vol. 12(3), pp. 317-323.*
Bae Yoe Sik, et al. "Identification of novel chemoattractant peptides for human leukocytes", Blood. 2001. 1;97(9):pp. 2854-2862.
Kaneider Nicole C., et al "Reversing systemic inflammatory response syndrome with chemokine receptor pepducins", Nat Med. 2005. 11:pp. 661-665.
de Kruijf Petra, et al. "The collagen-breakdown product N-acetyl-Proline-Glycine-Proline (n-alpha-PGP) does not interact directly with human CXCR1 and CXCR2", European Journal of Pharmacology, vol. 643, pp. 29-33 (Available online Jun. 21, 2010).
Liu D., et al., "Rosiglitazone, an agonist of peroxisome proliferator-activated receptor gamma, reduces pulmonary inflammatory response in a rat model of endotoxemia", Inflamm Res. 2005.54(11): pp. 464-470.
Wang J., et al., "Increased in vivo apoptosis in cells lacking mitochondrial DNA gene expression", Proc Natl Acad Sci U S A. Mar. 27, 2001;98(7): pp. 4038-4043.
Yan J.J., et al., "Therapeutic effects of lysophosphatidylcholine in experimental sepsis", Nat Med. 2004. 10:pp. 161-167.

* cited by examiner

*Primary Examiner* — Julie Ha
*Assistant Examiner* — Erinne Dabkowski
(74) *Attorney, Agent, or Firm* — NSIP Law

(57) ABSTRACT

A therapeutic agent for treating an infectious or inflammatory disease, a pharmaceutical composition for treating an infectious or inflammatory disease, and a method of using a pharmaceutical composition are provided. The pharmaceutical composition includes a peptide ligand that binds with CXCR2 as an active component. The active component can be useful in preventing and treating infectious and/or inflammatory diseases, including sepsis and septic shock by promoting the removal of bacteria by phagocytosis, suppressing an inflammatory response, and suppressing the apoptosis of immune cells.

3 Claims, 16 Drawing Sheets

SEQUENCE LISTING

```
<160> NUMBER OF SEQ ID NOS: 1

<210> SEQ ID NO 1
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term pal

<400> SEQUENCE: 1

Arg Thr Leu Phe Lys Ala His Met Gly Gln Lys His Arg
1               5                   10
```

COMPOSITION CONTAINING PEPTIDE LIGAND THAT BONDS WITH CXCR2 FOR TREATING INFECTIVE AND INFLAMMATORY DISEASES

CROSS-REFERENCE TO RELATED APPLICATION(S)

This application is a national stage of International Application No. PCT/KR2011/007807, filed Oct. 19, 2011, claiming priority based on Korean Patent Application No. 10-2010-0103259 filed Oct. 22, 2010, the entire disclosures of both of which are incorporated herein by reference for all purposes.

SEQUENCE LISTING

The instant application contains a Sequence Listing which has been submitted electronically in ASCII format and is hereby incorporated by reference in its entirety. Said ASCII copy, created on Dec. 24, 2013, is named 042099.0005_SL.txt and is 701 bytes in size.

BACKGROUND

1. Field

The present invention relates to a therapeutic agent, and for example to a therapeutic composition of infectious or inflammatory diseases including peptide ligand that bonds with CXCR2 as an active component.

2. Description of Related Art

Infectious diseases include infections by viruses, bacteria, parasites, etc., and among these, bacterial infection diseases have been treated by antibiotics, but the recent abuse of antibiotics have created various super bacteria, and thus, seeking new treatment strategies on bacterial infection diseases are necessary. Inflammatory diseases are associated with failure in controlling immune response, which includes atopic dermatitis, asthma, arthritis, etc. These diseases are showing rapid increase regardless of age or sex which requires effective treatment with few side effects.

Sepsis is a complicated clinical syndrome that is general in intensive care unit, which is caused by host response that is harmful for infection and causes damage. It has been reported that more than 200,000 people died from sepsis in the United States. Moreover, severe sepsis and septic hack have remarkably increased over the past two decades. Since the death rate of severe sepsis and septic shock is high, developing a novel effective therapeutic agent for sepsis is desperate.

Death rate due to sepsis is associated with the failure in controlling inflammatory response, and this failure is caused by critical defect in the innate immune system. Excessive apoptosis of lymphocytes appears in sepsis, which results in paralysis of various organs. In an initial stage of sepsis, some pro-inflammatory cytokine including TNF-a and IL-1B remarkably increases and causes overall defunctionalization on host immune system. Furthermore, it has been known that aggressive bacteria plays a main role in the progress and the outbreak of sepsis. Therefore, it is appropriate to focus on developing an effective method on controlling bacteria by promoting activities of phagocytes, suppressing production of pro-inflammatory cytokines, and blocking apoptosis of immune cells.

CXCR2 is a receptor for a typical chemoattractant that is found in phagocytes such as neutrophils, monocytes and macrophages. In human beings, CXCL8 bonds to CXCR2. Although mouse homologue of CXCL8 does not exist, its function can be replaced with other chemokines from mouse that include CXCL1. In vitro activation of CXCR2 by CXCL8 or KC induces leukocyte chemotactic movement in neutrophils and monocytes. It has been discovered that expression of not CXCR1 but CXCR2 is controlled downward by 50% compared to normal control in a neutrophils of a sepsis patient. The down-regulation of CXCR2 leads to a failure of neutrophil activation caused by a CXCR2 ligand. There is a report that injection of a CXCR2 blocking antibody increases the survival rate in a sepsis experimental model. Moreover, the deficit of CXCR2 was reported to increase the survival rate. Exposure of CXCL8 causes defuntionalization of endothelial cells and collapse in normal anticoagulation of endothelia. Kuliopulos et al. demonstrated that administration of a novel pepducin (x1/2pal-3: pal-RTLFKAH-MGQKHR (SEQ ID NO: 1)) ligand derived from an intracellular region of CXCR2 results in a remarkable increase in survival rate of cecal ligation and puncture (CLP)-septic mice by blocking a CXCR2-mediated signaling pathway by means of CXCL8 or CXCL1.

SUMMARY

In one general aspect, there is provided a pharmaceutical composition for treating an infectious or inflammatory disease, including a peptide ligand that binds with CXCR2 as an active component.

The peptide ligand that binds with CXCR2 may be acetylated-Pro-Gly-Pro (Ac-PGP).

The infectious or inflammatory disease may be sepsis or septic shock.

The active component may promote removal of bacteria by phagocytosis.

The active component may suppress an inflammatory response.

The active component may suppress apoptosis of immune cells.

The pharmaceutical composition may further include a pharmaceutically available carrier, excipient or diluent.

The pharmaceutical composition may be formulated for subcutaneous injection.

The pharmaceutical composition may be administered at an effective amount of 1 to 200 mg per 1 kg of body weight.

In another general aspect, there is provided a method of using a pharmaceutical composition to treat an infectious or inflammatory disease, involving: administering a pharmaceutical composition comprising a peptide ligand that binds with CXCR2.

In the general aspect of the method, the infectious or inflammatory disease may be sepsis or septic shock.

In the general aspect of the method, the pharmaceutical composition may be administered by a subcutaneous injection.

In the general aspect of the method, the pharmaceutical composition may be administered at an effective amount of 1 to 200 mg per 1 kg of body weight.

Other features and aspects may be apparent from the following detailed description, the drawings, and the claims.

DETAILED DESCRIPTION

Figure 1:
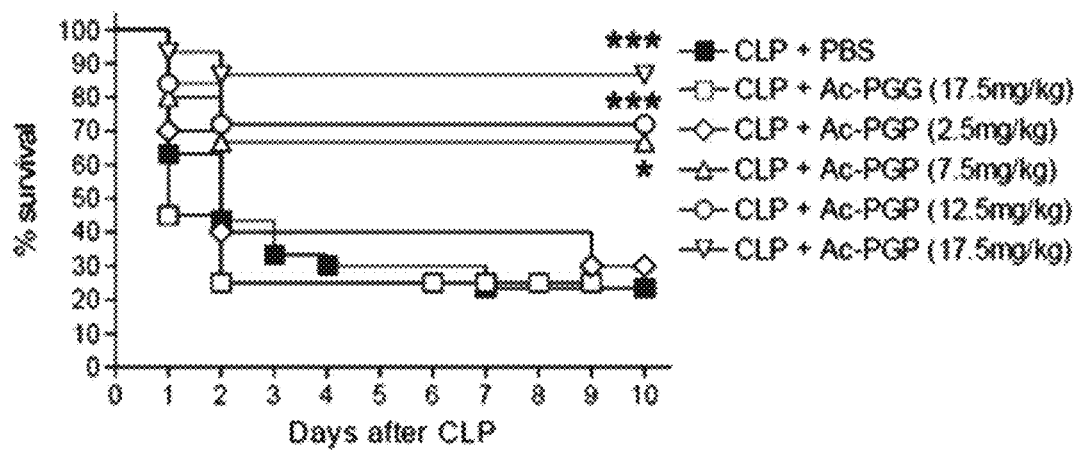
FIG. 1 shows a survival rate according to a concentration of Ac-PGP after the Ac-PGP is injected at various doses to CLP mice.

The following detailed description is provided to assist the reader in gaining a comprehensive understanding of the methods, apparatuses, and/or systems described herein. Accordingly, various changes, modifications, and equivalents of the systems, apparatuses and/or methods described herein will be suggested to those of ordinary skill in the art. Also, descriptions of well-known functions and constructions may be omitted for increased clarity and conciseness.

Technical Problem

While the present inventor was searching for a material that can enhance the effect of removing bacteria, suppressing inflammatory response and apoptosis of immune cell, identified that peptide ligand binding with CXCR2, especially Ac-PGP, satisfies the upper requirements and thus can effectively treat infectious or inflammatory diseases such as sepsis, and finally reached to the present invention.

Technical Solution

The present invention relates to a pharmaceutical composition for treating infectious or inflammatory disease including peptide that bonds with CXCR2 as an active component.

The peptide ligand that bonds with CXCR2 desirably refers to Ac-PGP.

The infectious or inflammatory disease may refer to sepsis or septic shock.

The active component according to the present invention promotes removal or disinfection of bacteria through phagocytosis by promoting production of reactive oxygen species such as hydrogen peroxide in phagocytes.

Also, the active component promotes production of Th1 cytokines (for example, IFN-γ, IL-12, and IL-2) and the IFN-γ suppresses inflammatory response by suppressing production of pro-inflammatory cytokines (for example TNF-α, IL-1β, and IL-6).

In addition, the active component suppresses apoptosis of immune cells such as splenocytes and thymocytes.

The pharmaceutical composition according to the present invention may further include a pharmaceutically available carrier, excipient or diluent.

The pharmaceutical composition according to the present invention may be formulated for subcutaneous injection.

The pharmaceutical composition according to the present invention is advisable to be administrated at an effective amount of 1 to 200 mg per 1 kg of body weight.

Advantageous Effects

According to the present invention, the peptide ligand binding with CXCR2, especially Ac-PGP, can be useful in effectively preventing and treating various infectious or inflammatory diseases including sepsis and septic shock by promoting removal of bacteria by phagocytosis, reducing production of inflammatory cytokines to suppress an inflammatory response, and suppressing apoptosis of immune cells.

EXAMPLES

The present invention is directed to a pharmaceutical composition for treating an infectious or inflammatory disease, which includes a peptide ligand binding with CXCR2 as an active component.

The active component of the present invention, "peptide ligand binding with CXC-chemokine receptor 2 (CXCR2)", means any peptide that bonds to CXCR2 and controls its functions which may be Ac-PGP.

The active component of the present invention, the Ac-PGP is a tripeptide in which amino acids, for example, proline (P; Pro), glycine (G, Gly) and proline are sequentially connected by means of an amide bond, where the proline is acetylated (Ac). The Ac-PGP is a degradation product of an extracellular matrix, and thus may be obtained by degrading a natural extracellular matrix, or connect respective amino acids by amide binding and acetylate to artificially synthesize.

According to one exemplary embodiment of the present invention, survival rate was increased when Ac-PGP was administered in a CLP animal model of sepsis. Especially when the Ac-PGP was administered 4 to 5 times at a concentration of 17.5 mg/kg, the highest increase in survival rate is observed.

According to another exemplary embodiment of the present invention, when the Ac-PGP was administered in the animal model of sepsis, inflammation in major internal organs (liver, lungs, and thymus) was suppressed. Also, the Ac-PGP suppressed apoptosis of immune cells such as splenocytes and thymocytes.

According to still another exemplary embodiment of the present invention, when the animal model of sepsis, or neutrophils phagocytizing E. coli, was treated with Ac-PGP, a bacteria removal effect was exhibited and such removal effect was mediated by hydrogen peroxide while hydrogen peroxide was increasingly produced by Ac-PGP, such increase in hydrogen peroxide was offset by CXCR2 antagonist.

According to still another exemplary embodiment of the present invention, when the animal model of sepsis, or neutrophils stimulated with LPS, was treated with Ac-PGP, it has been identified that production of the pro-inflammatory cytokine was inhibited.

According to still another exemplary embodiment of the present invention, the Ac-PGP enhances production of the Th1 cytokines (IFN-$\gamma$, IL-12, and IL-2), and the IFN-$\gamma$ suppresses production of the pro-inflammatory cytokines such as TNF-$\alpha$ and IL-6. However, the effect of the Ac-PGP on apoptosis of lymphocytes was offset in IFN-$\gamma$-deficient mice.

According to yet another exemplary embodiment of the present invention, it revealed that the therapeutic effect of the Ac-PGP on sepsis was mediated by CXCR2.

As described above, the Ac-PGP belonging to a family of peptide ligands binding with CXCR2 may be used as a therapeutic agent for treating various infectious or inflammatory diseases, especially sepsis or septic shock, by promoting removal of bacteria by phagocytosis, and suppressing an inflammatory response and apoptosis of immune cells.

In the present invention, the term "infectious disease" refers to all kinds of diseases caused by infection of microorganisms such as viruses, bacteria, molds, and parasites, preferably diseases caused by infection of bacteria.

In the present invention, the term "inflammatory disease" refers to diseases associated with a failure in the control of an immune response, for example, atopic dermatitis, asthma, various allergic diseases, diabetes, arthritis, irritable bowel syndrome, ulcerative colitis, inflammatory bowel disease, etc., but the present invention is not limited thereto.

The pharmaceutical composition according to the present invention may further include a carrier, excipient or diluent generally used in the related art.

The pharmaceutical composition according to the present invention can be used formulated into oral administrative formulation such as powder, granule, tablet, capsule, suspension, emulsion, syrup, or aerosol, sterile injectable solution, a suppository, and a preparation for percutaneous administration. The pharmaceutically available carrier, excipient and diluent that may be included in the composition may include lactose, dextrose, sucrose, sorbitol, mannitol, xylitol, erythritol, maltitol, starch, acacia gum, alginate, gelatin, calcium phosphate, calcium silicate, celluose, methyl celluose, microcrystalline celluose, polyvinylpyrrolidone, water, methylhydroxybenzoate, propylhydroxybenzoate, talc, magnesium stearate, and a mineral oil. Upon demands, the pharmaceutical composition may be formulated using a diluent or excipient such as a filler, a bulking agent, a binder, a wetting agent, a disintegrating agent, or a surfactant.

According to one exemplary embodiment, the pharmaceutical composition according to the present invention may be formulated into a solid preparation for oral administration. The solid preparation for oral administration may include a tablet, a pill, powder, granule, a capsule, etc., and in this case, the solid preparation is formulated by mixing at least one excipient, for example, starch, calcium carbonate, sucrose or lactose, gelatin, etc. with the extract. Also, lubricants such as magnesium stearate and talc may be used besides the simple excipient.

According to another exemplary embodiment, the pharmaceutical composition including the active component of the present invention may be formulated into a liquid preparation for oral administration. The liquid preparation for oral administration includes a suspension, a liquid for internal use, an emulsion, syrup, etc., and such liquid preparation contains various excipients, in general for example, a wetting agent, a sweetening agent, an aromatic, and a preservative, in addition to an inert diluent (for example, purified water, ethanol, or liquid paraffin) typically used in the related art.

According to still another exemplary embodiment, the pharmaceutical composition including the active component according to the present may be formulated into a preparation for parenteral administration, preferably intraperitoneal administration. The preparation for parenteral administration includes a sterilized aqueous solution, a water-insoluble solvent, a suspension, an emulsion, a lyophilized preparation, and a suppository. A proper buffer solution such as a Hank's solution, Ringer's solution, or a physically buffered saline may be used as the sterilized aqueous solution. Among the water-insoluble solvents, propylene glycol, polyethylene glycol, a vegetable oil such as olive oil, or an injectable ester such as ethyl oleate may be used as the suspension. Upon demands, a preservative, a stabilizing agent, a wetting agent, an emulsifying agent, or a salt and/or buffer for osmotic regulation may be used herein. Meanwhile, Witepsol, Macrogol, Tween 61, cacao butter, laurinum, or glycerol gelatin may be used as the suppository.

The composition formulated according to the above-described method may be administered at an effective dose through various routes of administration including oral or parenteral administration (percutaneous, subcutaneous, intravenous, intramuscular, intraperitoneal injection, etc.). As used herein, the term "effective dose" refers to a dose of a composition (that is, an amount of an active component) exhibiting a preventive or therapeutic effect when administered to a patient. A dosage of the composition according to the present invention may be properly selected according to a route of administration, a subject to be administered, the age, sex and body weight of a patient, an individual difference, and the severity of a disease. Preferably, the active component included in the composition of the present invention may vary according to the severity of a disease, but may be administered at an effective dose of 1 to 200 mg, more preferably 5 to 100 mg, and most preferably 10 to 50 mg per 1 kg body weight. The administration may be performed 1 to 10 times, preferably 3 to 6 times, and more preferably 4 to 5 times.

Hereinafter, the present invention will be described in further detail with reference to the following preferred Examples. However, it should be understood that the following Examples are given by way of illustration of the present invention only, and are not intended to limit the scope of the present invention, as apparent to those skilled in the art.

Example 1

Materials and Methods

1. Animal and Sepsis Model

Male WT ICR mice were used to evaluate a therapeutic effect of Ac-PGP. IFN-γ-deficient mice (kindly provided by Y. K. Kim at the Pohang University of Science and Technology, Pohang, Republic of Korea) were used for mechanism study. All Examples in which animals were used were performed according to the instructions with permission of the Institutional Review Board (IRB) for the care and management of laboratory animals at Dong-A University. In the case of the CLP, mice were anesthetized with pentothal sodium (50 mg/kg, intraperitoneally injected), and abdomen of each mouse was cut along a central cutting line to expose an appendix. Then, an ileocecal valve of the appendix was tied up, both surfaces of the ileocecal valve were punctured twice with a 22-gauge needle (or punctured once to measure a production amount of cytokines), and the abdomen was sutured. Sham CLP mice were treated in the same manner as described above, except that CLP of the appendix was not performed. A survival rate of the mice was monitored every day for 10 days. In the case of the LPS or $E.$ $coli$ model, $E.$ $coli$ and LPS were intraperitoneally injected at concentrations of $1 \times 10^9$ cells/mouse and 60 mg/kg, respectively. A survival rate of the mice was monitored once a day for 10 days.

2. Measurement of In Vivo Disinfection Activity

A peritoneal lavage fluid was collected 24 hours after CLP, and incubated at 37° C. overnight in a blood agar base plate (trypticase soy agar Deeps, Becton Dickinson). The number of colony forming units (CFUs) was counted according to a method disclosed in Yan J J et al. 2004 Nat. Med. 10:161-167.

3. Quantification of Pulmonary Edema

A level of pulmonary edema was quantified by evaluating a W/D weight ratio of a lung according to a method disclosed in Liu D. et al. 2005 Inflamm. Res. 54:464-470. A total of the collected wet lung were weighed, and kept at 60° C. for 48 hours in an oven. Then, the weight of the dried lung was measured, and W/D weight ratio of the dried lung was calculated.

4. Histological Analysis

A mouse was subjected to CLP surgery, and after 2 hours, PBS or Ac-PGP was injected at a dose of 17.5 mg/kg to the mouse. After the CLP surgery, the mouse was sacrificed within 24 hours, and the lung of the mouse was fixed, microtomed, and stained with hematoxylin and eosin so as to perform morphological analysis.

5. Immunohistochemistry for Evaluation of Apoptosis

First, a tissue embedded in paraffin was deparaffinized using a typical histological protocol, and performed digoxigenin-dUTP nick end labeling (TUNEL) analysis. Sections were permeated into the Triton X-100 at 4° C. for 2 minutes, and the sections were flooded in terminal deoxynucleotidyl transferase (TdT) and a TUNEL reagent at 37° C. for 60 minutes. A percentage of apoptotic cells (TUNEL-positive cells) was determined by counting 500 splenocytes under an optical microscope. Also, the tissue embedded in paraffin was deparaffinized using a typical histological protocol, and immunohistochemical analysis was performed on the microtomed sections of caspase-3 (Wang J. et al. 2001 Proc. Natl. Acad. Sci. USA 98:4038-43).

6. Separation of Mouse Neutrophils and Measurement of $H_2O_2$

Mouse neutrophils were separated from peripheral blood using a Histopaque-1077 solution (Sigma) (Bae Y S et al. 2001 Blood. 97: 2854-2862). The neutrophils separated from normal mice were stimulated with various concentrations of Ac-PGP for 10 minutes in the presence of cytochalasin B (5 μM). To identify the role of mCXCR2, the neutrophils were pre-incubated in various concentrations of SB225002 or a vehicle (DMSO) for 30 minutes in a stationary environment, and Ac-PGP (20 μM) was added, and incubated for 10 minutes. $H_2O_2$ in a supernatant was measured using a $H_2O_2$ measurement kit (Molecular probe).

7. Separation of Human Neutrophil and PBMCs

All kinds of protocols used in human beings were approved by the Institutional Review Board (IRB) at Dong-A University Hospital, and prior consents were obtained from all blood donors. Peripheral blood was collected from healthy donors, and human peripheral monocytes were separated using a Histopaque-1077 gradient. Neutrophils were separated through methods such as dextran precipitation of red blood cell, hypotonic lysis, and usage of lymphocyte isolation medium gradient, as known in the related art (Bae, Y. S. et al. Blood 97, 2854-2862(2001)). The separated human leukocytes were used immediately.

8. Disinfection Activity of Neutrophils

The disinfection activities of the neutrophils were measured according to a method disclosed by Yan et al. (Yan J J et al. 2004 Nat. Med. 10:161-167). The neutrophils were stationarily incubated at 37° C. for an hour on a 13 mm plastic cover slip in a 60 mm plastic culture dish. The non-attached cells were removed by PBS. The attached neutrophils were stationarily incubated for an hour with $10^6$ opsonized $E.$ $coli$ cells. The non-phagocytized $E.$ $coli$ cells were washed, and the number of bacteria surviving in the neutrophils was determined before and after the $E.$ $coli$ cells were treated with various concentrations of Ac-PGP or vehicle for an hour. A percentage of the apoptosized bacteria was calculated as follows.

100×(1−CFU Number after stimulus with Ac-PGP/
CFU Number before stimulus with Ac-PGP)

9. Measurement of Cytokines After CLP

To measure a production amount of cytokines induced by CLP in a peritoneal lavage fluid, mice were provided with Ac-PGP for 2 hours, 14 hours, 26 hours, and 38 hours after CLP. A peritoneal lavage fluid was collected within various time zones between 4 and 72 hours after the CLP, and cytokines present in the peritoneal fluid was measured using ELISA (BD Biosciences Pharmingen).

10. Release of Cytokines from In Vitro Inflammatory Cells

Mouse splenocytes were positioned on an RPMI 1640 medium including 5% FBS in a 96-well plate, and maintained at 37° C. in a 5% $CO_2$ incubator. Thereafter, the splenocytes were stationarily incubated with LPS (100 ng/ml) for 24 hours in the presence or absence of Ac-PGP. After 30 minutes, LPS was added to the cells and collected a cell-free supernatant, and then the supernatant was centrifuged, and TNF-α, IL-6 and IFN-γ were measured using ELISA (BD Biosciences Pharmingen). In regards to the effect of IFN-γ on production of pro-inflammatory cytokines induced by LPS, $5 \times 10^5$ cells/ml of the mouse splenocytes were stimulated with 100 ng/ml of LPS in the presence or absence IFN-γ (R&D) (at various concentrations of 1, 10, 100 and 1,000 IU/ml). Amounts of TNF-α and IL-6 were measured 20 hours after stationary incubation using ELISA (BD Biosciences Pharmingen).

Example 2

Results

1. Ac-PGP Prevents Death Induced by Sepsis

Figure 2:
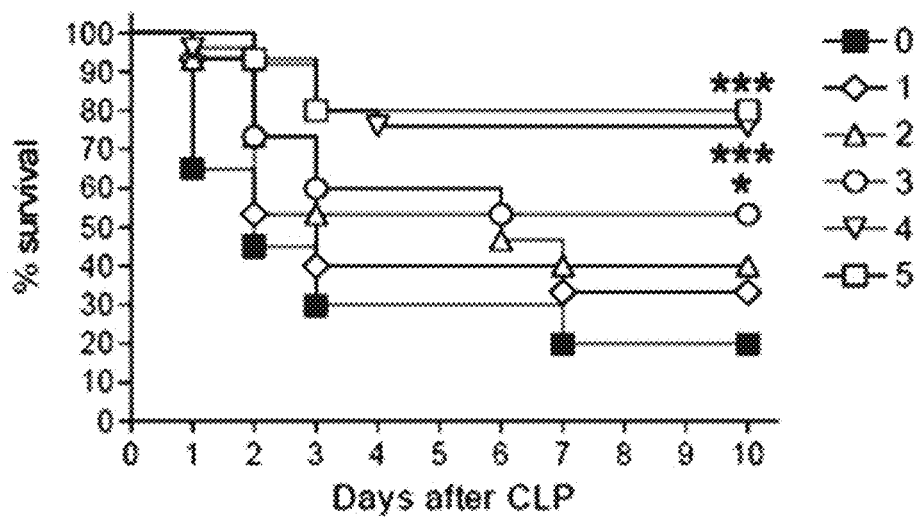
FIG. 2 shows a survival rate according to the number of recoveries after Ac-PGP is recovered from CLP mice several times.
Figure 3:
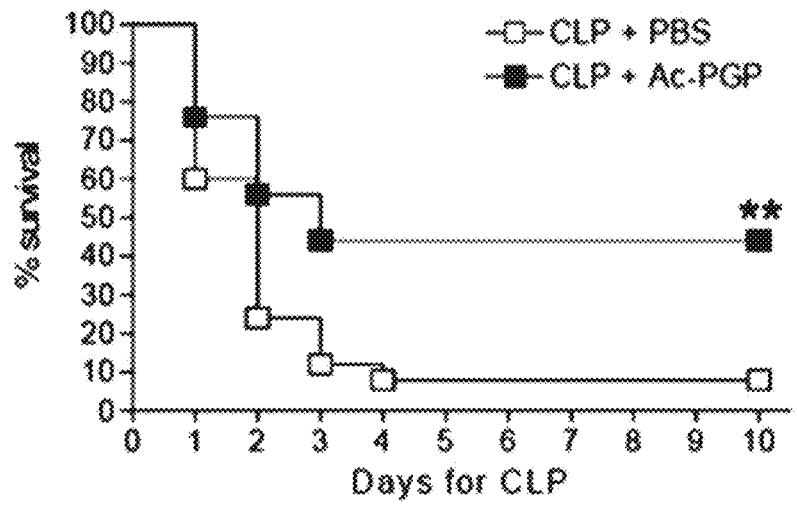
FIG. 3 shows a survival rate when CLP mice are vaccinated four times with Ac-PGP at a concentration of 17.5 mg/kg.

An experimental therapeutic effect of Ac-PGP on sepsis was examined in CLP using albino Institute of Cancer Research (ICR) mice. Survival of the mice was monitored for 10 days after CLP. On the second day after the CLP, only 20% of untreated WT mice survived (FIG. 1). Subcutaneous administration of Ac-PGP in 2 hours after the CLP remarkably increased the survival rate in a dose-dependent manner (FIG. 1). Injection of 7.5, 12.5 or 17.5 mg/kg of Ac-PGP remarkably increased survival of the mice, compared with the PBS-injected control (FIG. 1). In regard with the cycle of injection, the survival rate was highly increased when 17.5 mg/kg of Ac-PGP was injected 3 or 4 times 2 hours after the CLP at an interval of 12 hours (FIG. 2). Based on these results, 17.5 mg/kg of the Ac-PGP was injected three times additionally into CLP mice at an interval of 12 hours, starting from 2 hours after the CLP. Even when the Ac-PGP was injected 10 hours after the CLP, a therapeutic effect was still exhibited (FIG. 3).

Figure 4:
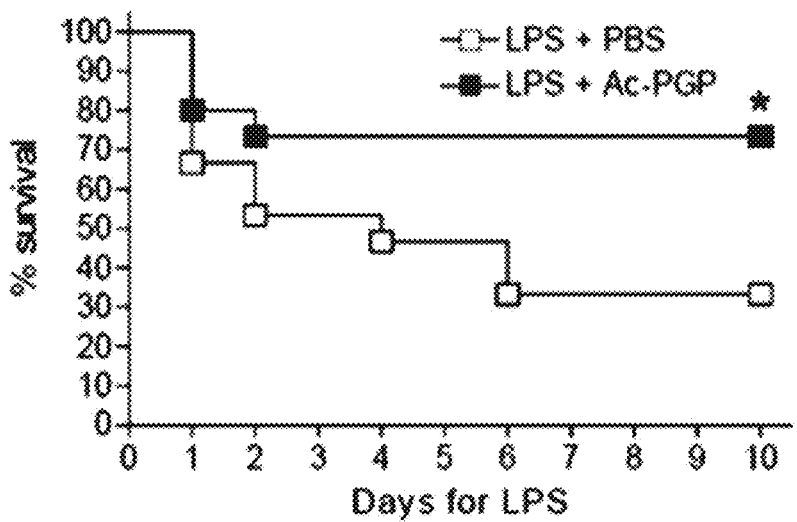
FIG. 4 shows a survival rate when sepsis mice vaccinated with LPS are vaccinated four times with Ac-PGP at a concentration of 17.5 mg/kg.

In another mouse model of sepsis, a therapeutic effect of Ac-PGP was also evaluated. When mice cells ($1 \times 10^9$ cells/mouse) vaccinated with *E. coli* were treated four times with 17.5 mg/kg of the Ac-PGP from 2 hours after the vaccination, a death rate decreased compared with the *E. coli*-vaccinated mice treated with PBS. Also, the Ac-PGP decreased mortality of the mice into which 60 mg/kg of LPS was intraperitoneally injected (FIG. 4).

Figure 5:
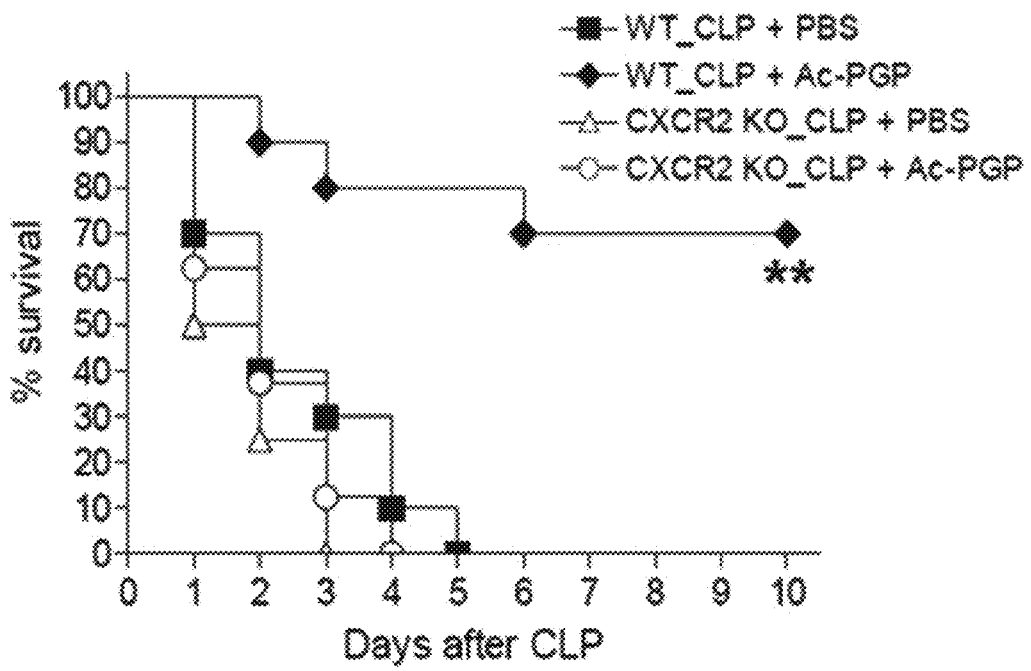
FIG. 5 shows a survival rate when CLP mice are treated with Ac-PGP after the CLP mice are pretreated or not pretreated with a CXCR2 antagonist (SB225002).
Figure 6:
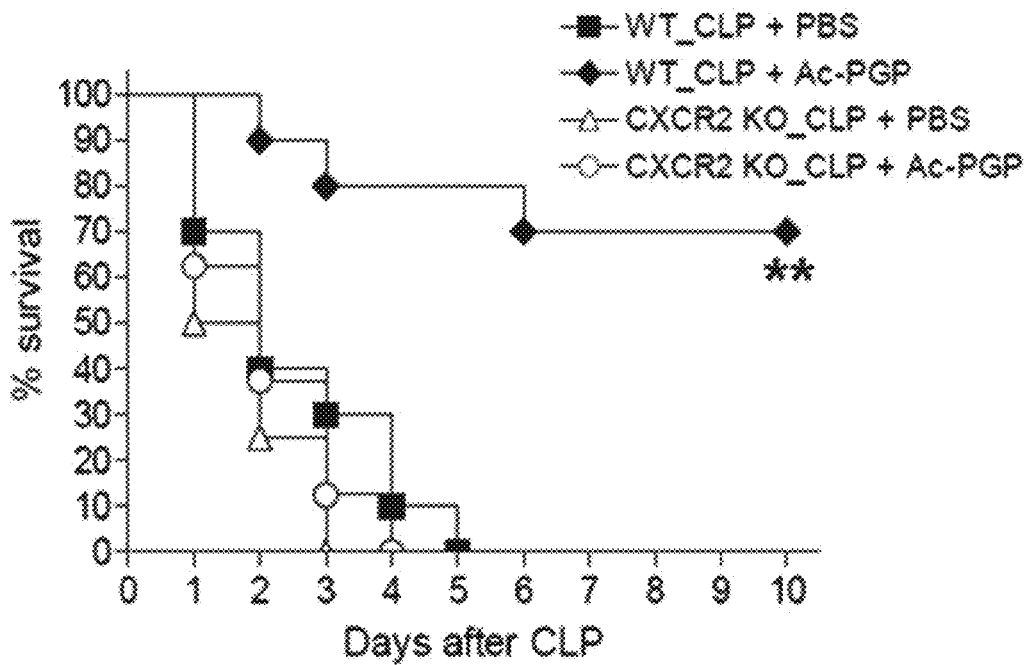
FIG. 6 shows a survival rate when wild-type CLP mice or CXCR2-deficient CLP mice are treated with Ac-PGP.

The Ac-PGP was evaluated to determine whether the antiseptic activity of Ac-PGP served through CXCR2 that was a known receptor of Ac-PGP. In the CLP mice pretreated with the CXCR2-selective antagonist (SB225002), the Ac-PGP could not improve the survival rate of the mice (FIG. 5). Ac-PGP treatment could not improve a survival rate in the CXCR2-deficient sepsis mice (FIG. 6). From these results, it was revealed that the Ac-PGP specifically functioned through CXCR2 to increase a survival rate in an experimental sepsis.

2. Ac-PGP Suppresses Inflammatory Response in Major Internal Organs and Apoptosis of Immune Cells

Figure 7:
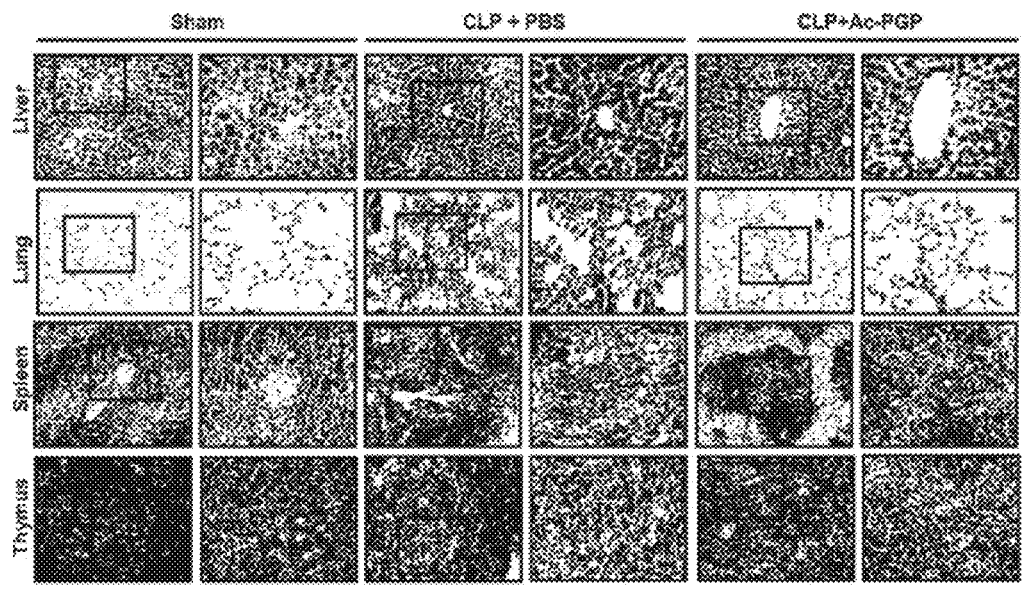
FIG. 7 shows an effect of Ac-PGP on inflammation of major internal organs caused by CLP.
Figure 8:
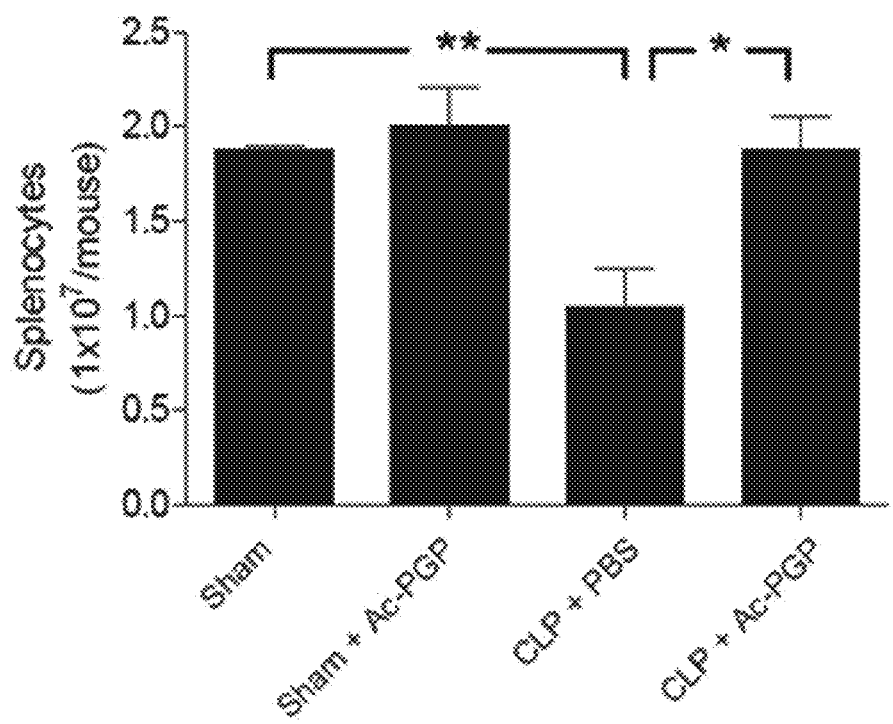
FIG. 8 shows an effect of Ac-PGP on apoptosis of splenocytes caused by CLP.
Figure 9:
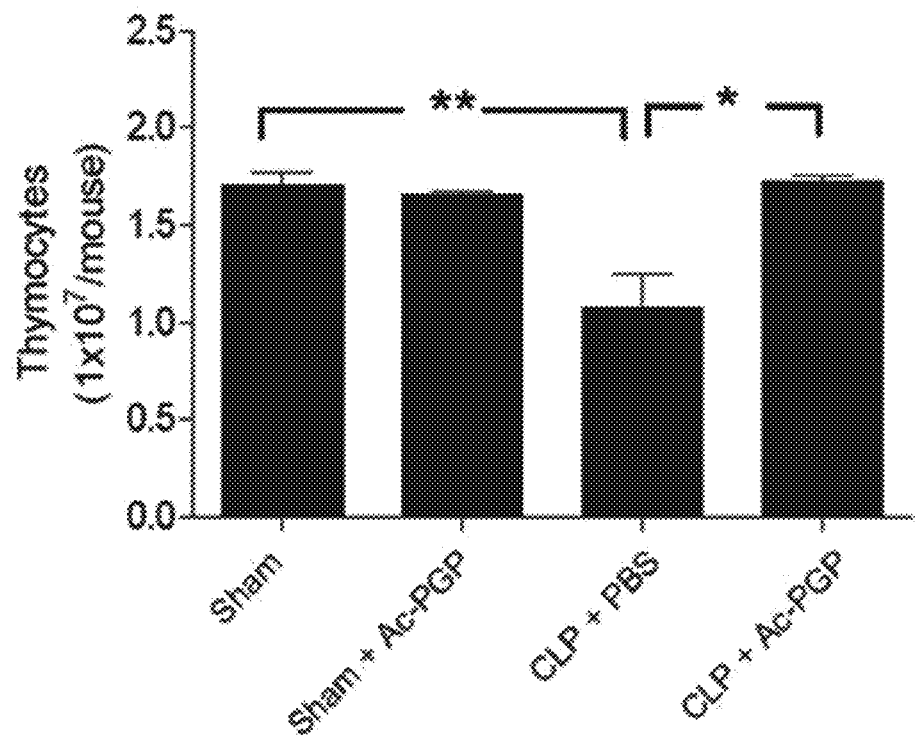
FIG. 9 shows an effect of Ac-PGP on apoptosis of thymocytes caused by CLP.

The defunctionalization of the major internal organs such as lungs was associated with the mortality after sepsis. A morphological change was observed by performing hematoxylin and eosin staining. As shown in FIG. 7, CLP induced significant inflammation in the major internal organs such as the liver, lungs and thymus. Liver tissues from the CLP mice were necrotized to a higher extent, but the necrosis of the liver tissues was decreased by administration of Ac-PGP. Severe alveolar congestion and wide thrombotic lesions were formed in the lungs from the CLP mice, but formation of the alveolar congestion and thrombotic lesions was also remarkably suppressed by the Ac-PGP. Administration of the Ac-PGP suppressed apoptosis of the thymus and spleen induced by the CLP. Most of the apoptosis in the thymus or spleen of a CLP mouse was caused in the cortex of the thymus or spleen in which immature cells were populated. When compared with those of the sham or Ac-PGP mice, an important morphological change in apoptotic cells of the CLP mice is that small compact pyknosis containing multiple nuclear fragments were present in apoptotic lymphocytes (FIG. 7). Administration of Ac-PGP strongly inhibited inflammation in the major internal organs induced by CLP. Also, it was revealed in this Example that the CLP induced an increase in a wet/dry (W/D) weight ratio of a lung which is an indicator of acute lung inflammation. The apoptosis of immune cells was also accompanied with sepsis. The sepsis by CLP induced the apoptosis of the immune cells in the spleen and thymus, but such an effect was remarkably suppressed by administration of the Ac-PGP (FIGS. 8 and 9).

3. Ac-PGP Promotes Bacteriocidal Effect

Figure 10:
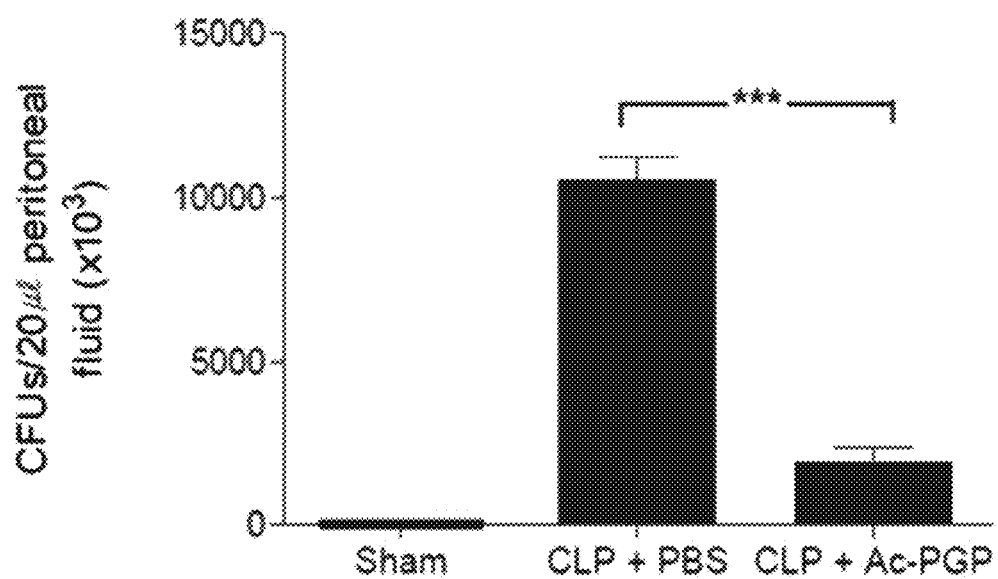
FIG. 10 shows a bacteriocidal effect of Ac-PGP on bacteria in peritoneal fluids of CLP mice.
Figure 11:
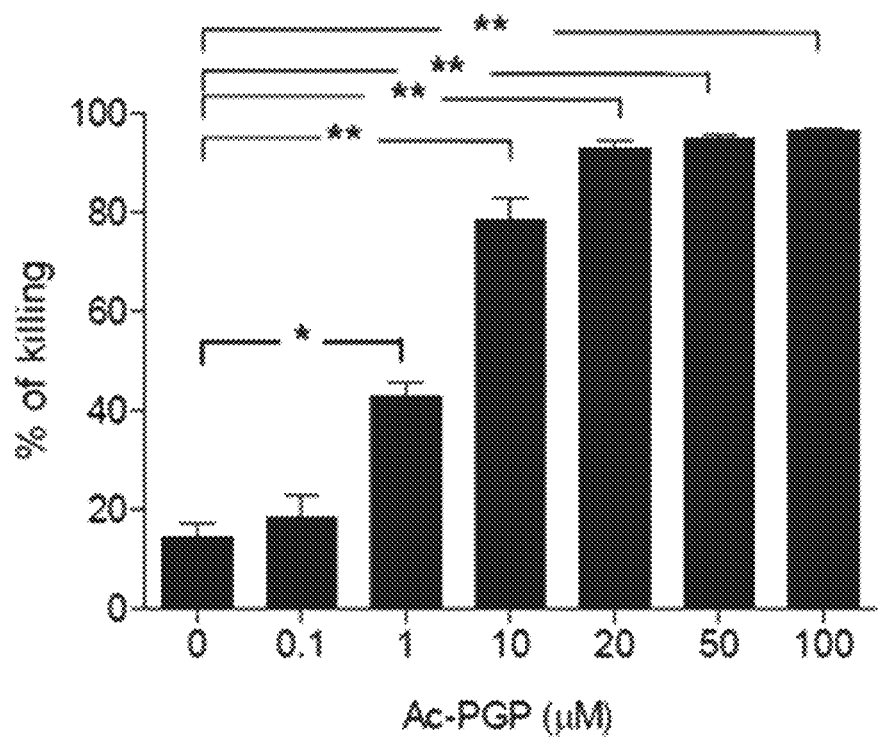
FIG. 11 shows a bacteriocidal effect of Ac-PGP on *Escherichia coli* in mouse neutrophils.
Figure 12:
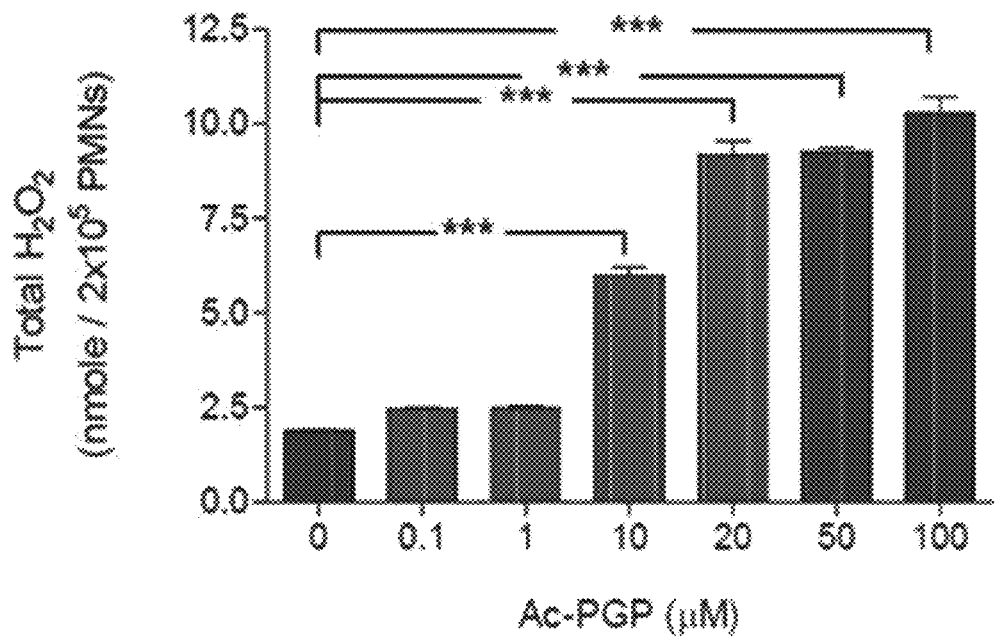
FIG. 12 shows a production amount of hydrogen peroxide in mouse neutrophils treated with various concentrations of Ac-PGP.
Figure 13:
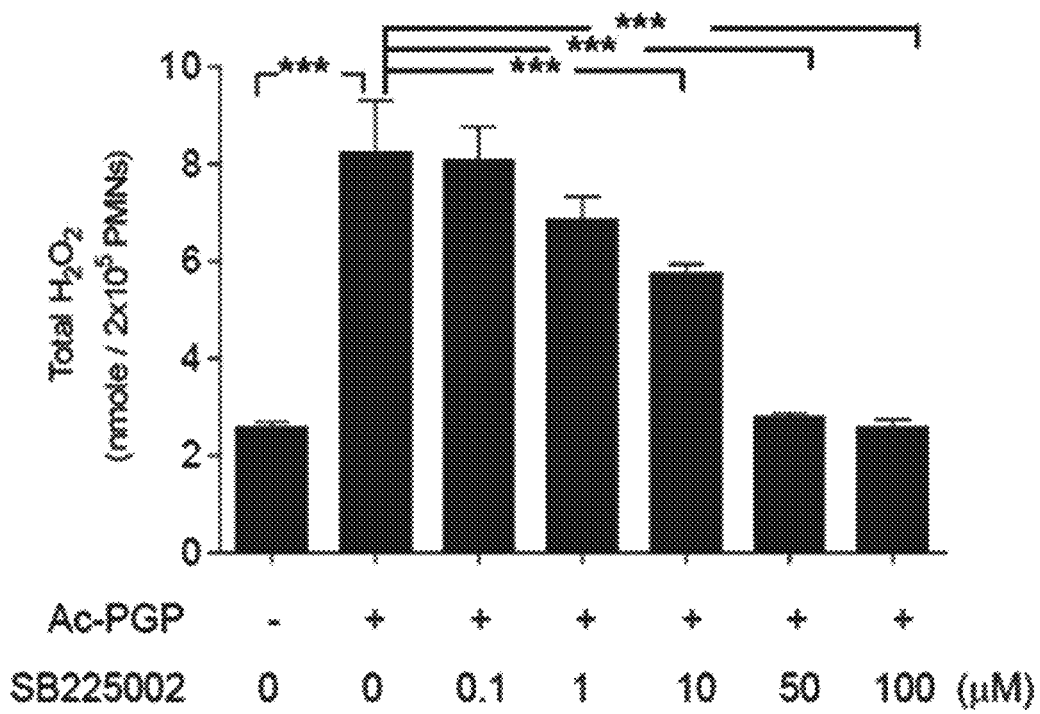
FIG. 13 shows a production amount of hydrogen peroxide when mouse neutrophils are treated with Ac-PGP under the condition of the mouse neutrophils pretreated or not pretreated with a CXCR2 antagonist(SB225002).

A death rate by CLP is correlated with the number of bacterial colonies in a peritoneal fluid. Therefore, an effect of the Ac-PGP on removal of bacteria in a peritoneal fluid was examined. Administration of the Ac-PGP remarkably reduced the number of bacterial colonies in the peritoneal fluid to 82.1% 24 hours after the CLP (FIG. 10). In vitro disinfection activity of the Ac-PGP was examined using neutrophils derived from a mouse. The mouse neutrophils were kept for an hour to phagocytize *E. coli*, and then stimulated with various concentrations of Ac-PGP (0.1 to 100 nM) for 20 minutes. The stimulation of the mouse neutrophil with the Ac-PGP highly increased the disinfection activity in a dose-dependent manner (FIG. 11). A reactive oxygen species such as hydrogen peroxide was known as an important molecule participating in the disinfection activity. Therefore, an effect of Ac-PGP on production of hydrogen peroxide in the mouse neutrophils was examined. The stimulation of the mouse neutrophils with various concentrations of the Ac-PGP strongly increased production of hydrogen peroxide in a concentration-dependent manner (FIG. 12). To examine a role of CXCR2 in production of hydrogen peroxide by the Ac-PGP, the mouse neutrophils were pretreated with a CXCR2 antagonist (SB225002) before they were treated with the Ac-PGP. The production of hydrogen peroxide by the Ac-PGP was completely suppressed by the CXCR2 antagonist (FIG. 13).

4. Ac-PGP Reduces Level of Pro-Inflammatory Cytokine in CLP Model

Figure 14:
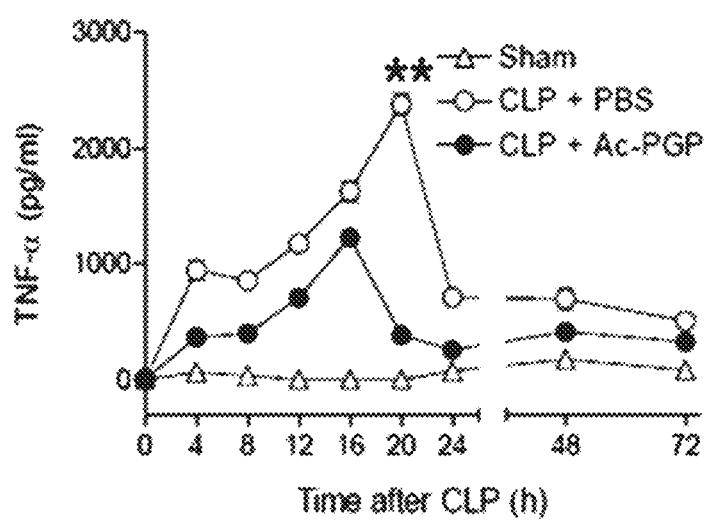
FIG. 14 shows an effect of Ac-PGP on a production amount of a pro-inflammatory cytokine, TNF-α, in CLP mice.
Figure 15:
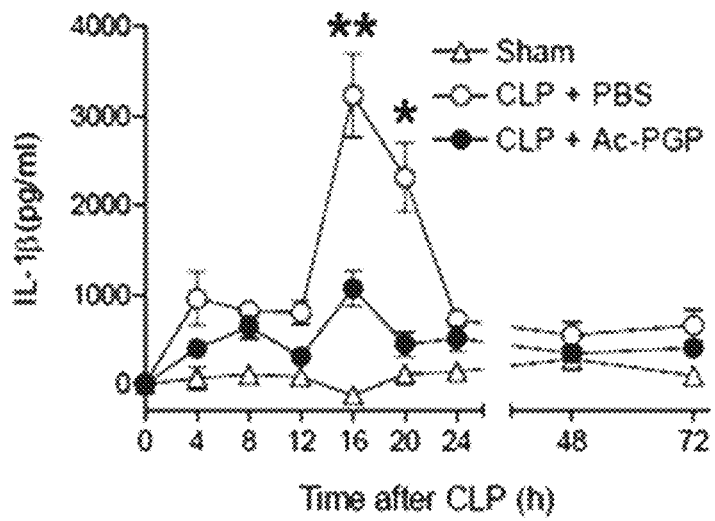
FIG. 15 shows an effect of Ac-PGP on a production amount of a pro-inflammatory cytokine, IL-1β, in CLP mice.
Figure 16:
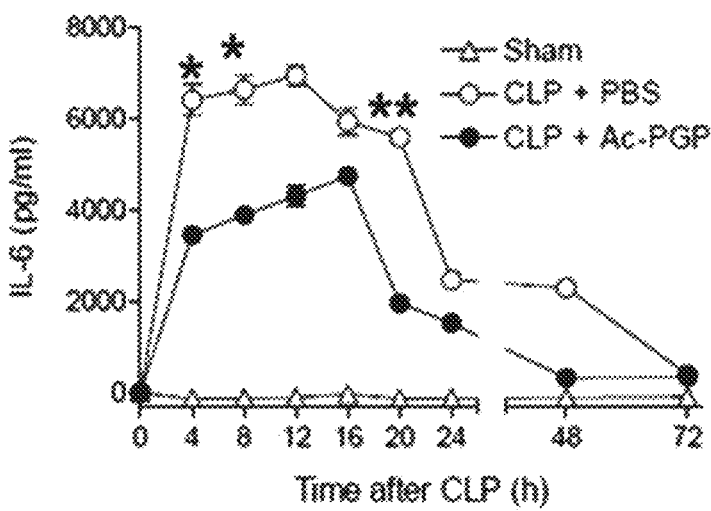
FIG. 16 shows an effect of Ac-PGP on a production amount of a pro-inflammatory cytokine, IL-6, in CLP mice.
Figure 17:
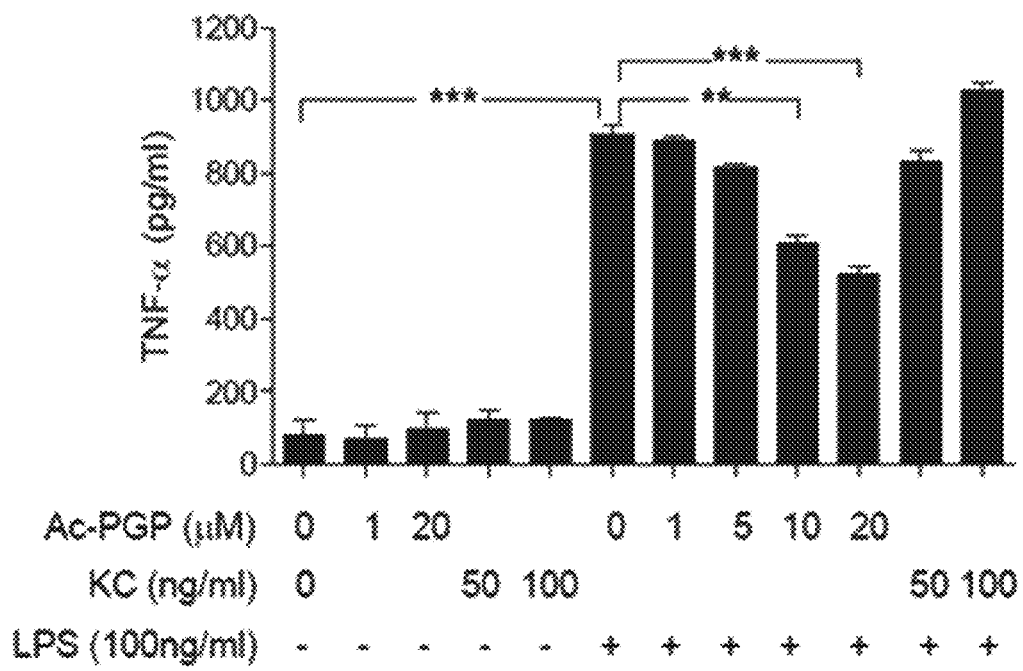
FIG. 17 shows an effect of Ac-PGP or KC on a production amount of a pro-inflammatory cytokine, TNF-α, in mouse splenocytes using LPS.
Figure 18:
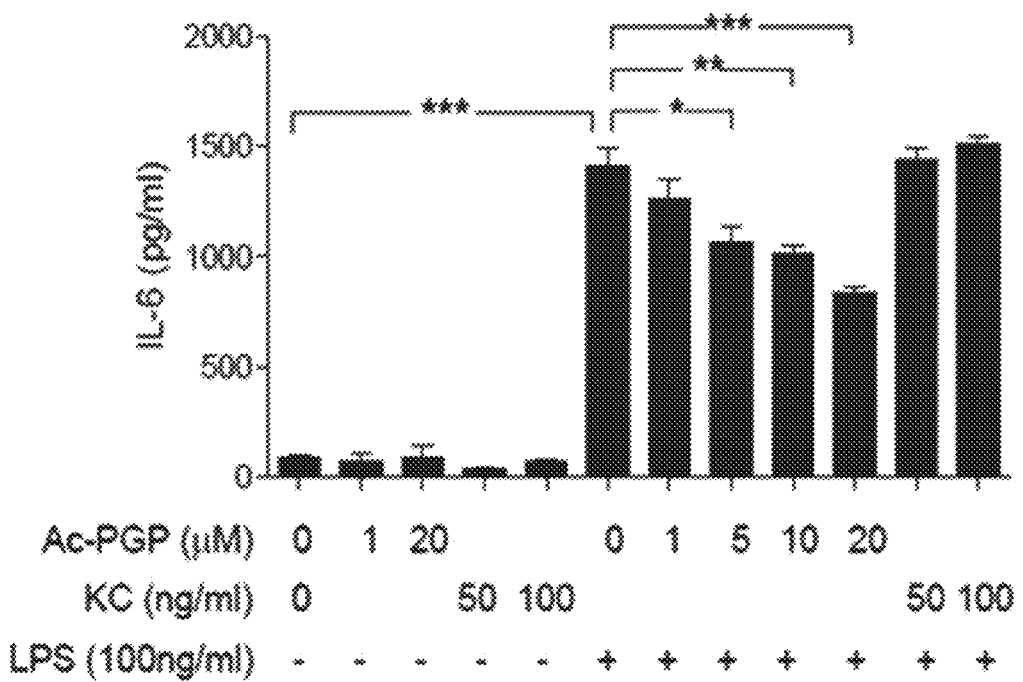
FIG. 18 shows an effect of Ac-PGP or KC on a production amount of a pro-inflammatory cytokine, IL-6, in mouse splenocytes using LPS.

An effect of the Ac-PGP on a pro-inflammatory cytokine in a peritoneal fluid by CLP was determined from 4 to 72 hours after the CLP. The CLP induced a remarkable increase in levels of pro-inflammatory cytokines (TNF-α, IL-1β and IL-6) within 24 hours (FIGS. 14 to 16). Injection of the Ac-PGP in a sepsis model by the CLP induced a remarkable change in levels of the cytokines. The injection of the Ac-PGP induced a decrease in levels of the pro-inflammatory cytokine (TNF-α, IL-1β and IL-6) (FIGS. 14 to 16). To evaluate an effect of the Ac-PGP on production of the pro-inflammatory cytokines by the LPS, in vitro production of TNF-α and IL-6 by the mouse splenocytes was evaluated. Direct release of the TNF-α and IL-6 from the mouse splenocytes by the LPS was suppressed by in vitro treatment with the Ac-PGP (FIGS. 17 and 18). However, KC which was a counterpart of mouse IL-8 could not suppress production of the TNF-α and IL-6 stimulated by the LPS (FIGS. 17 and 18).

5. Bacteriocidal Effect and Anti-Inflammatory Effect of Ac-PGP Depending on Pathway Mediated by Type 1 Cytokine (IFN-γ)

Figure 19:
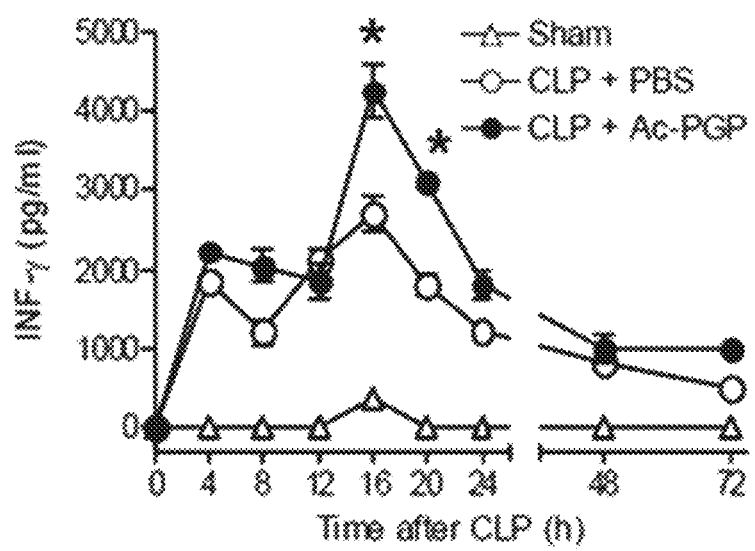
FIG. 19 shows an effect of Ac-PGP on a production amount of a type 1 cytokine, IFN-γ, in CLP mice.
Figure 20:
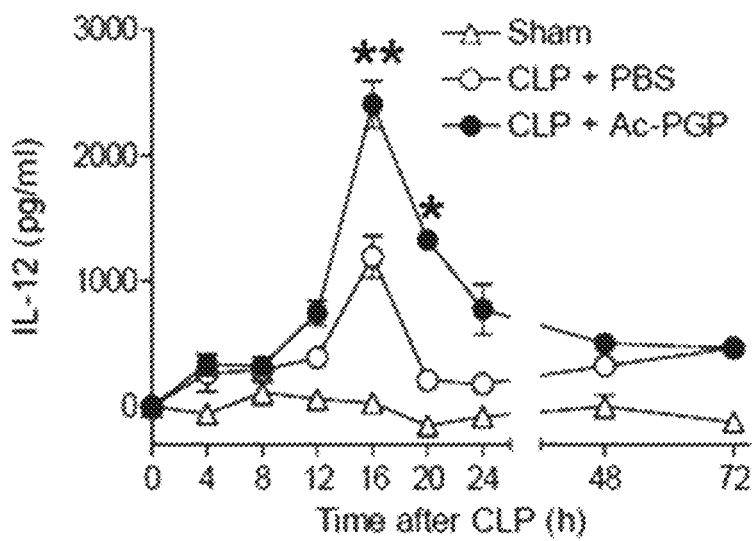
FIG. 20 shows an effect of Ac-PGP on a production amount of a type 1 cytokine, IL-12, in CLP mice.
Figure 21:
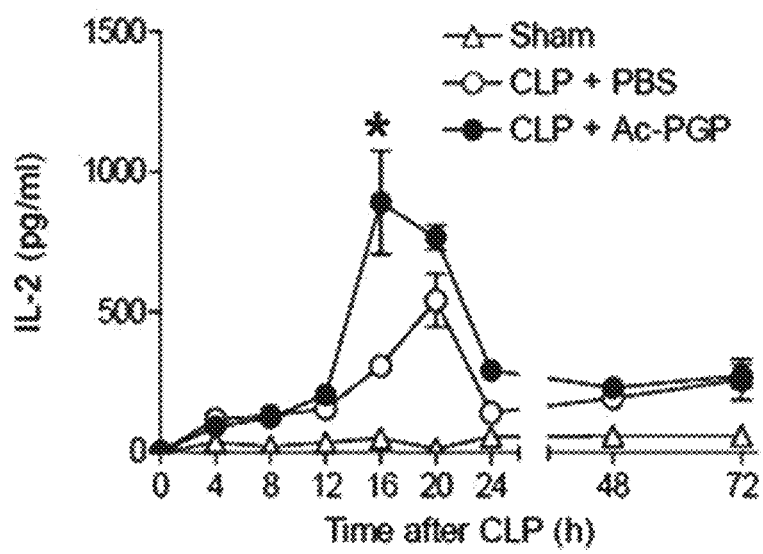
FIG. 21 shows an effect of Ac-PGP on a production amount of a type 1 cytokine, IL-2, in CLP mice.

An effect of the Ac-PGP on levels of Th1 cytokines by CLP in a peritoneal fluid was also determined from 4 to 72 hours after the CLP. The levels of T-helper type 1 cytokines (IFN-γ, IL-12p70 and IL-2) were remarkably increased immediately upon the injection of the Ac-PGP (FIGS. 19 to 21). Since the Ac-PGP improved levels of IFN-γ and IL-12 in the peritoneal fluid 24 hours after the CLP (FIGS. 19 to 21), the effect of the type 1 cytokines on the disinfection activity of the Ac-PGP was evaluated.

Figure 22:
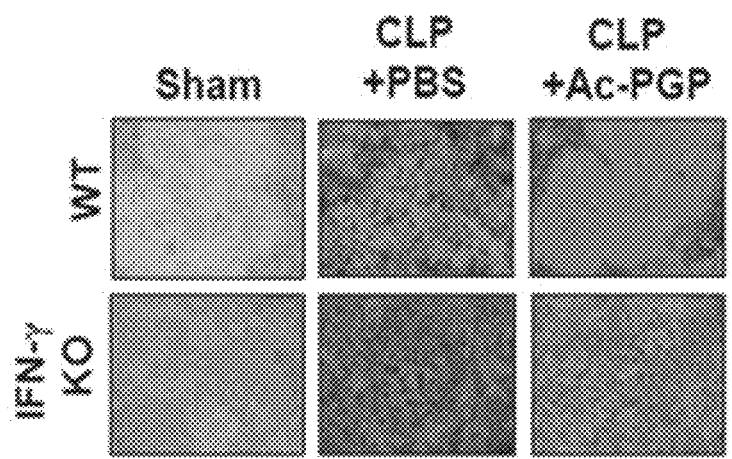
FIG. 22 shows an effect of Ac-PGP on apoptosis of splenocytes in IFN-γ-deficient CLP mice.
Figure 23:
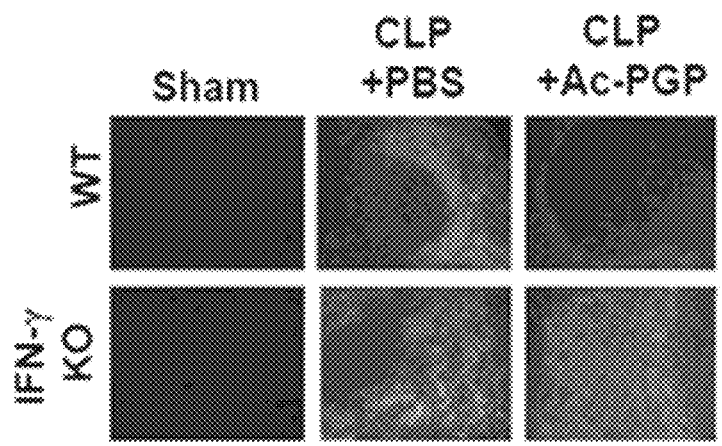
FIG. 23 shows an effect of Ac-PGP on activation of caspase-3 in splenocytes of CLP mice.

The apoptosis of immune cells is associated with the mortality on sepsis. Here, the CLP was proven to remarkably increase apoptosis of splenocytes (FIG. 22). Administration of Ac-PGP remarkably suppressed the apoptosis of splenocytes. However, the inhibitory effect of the apoptosis of splenocytes by Ac-PGP was remarkably relieved in IFN-γ-deficient mice (FIG. 22). Apoptosis of lymphocytes was induced by activation of some major caspases including caspase-3. Therefore, not only the effect of Ac-PGP on activation of caspase-3 but also the effect of CLP activation by caspase-3 were examined (FIG. 23). The activation of caspase-3 was observed in sepsis caused by the CLP. However, the activation of caspase-3 was remarkably suppressed by the Ac-PGP (FIG. 23).

Figure 24:
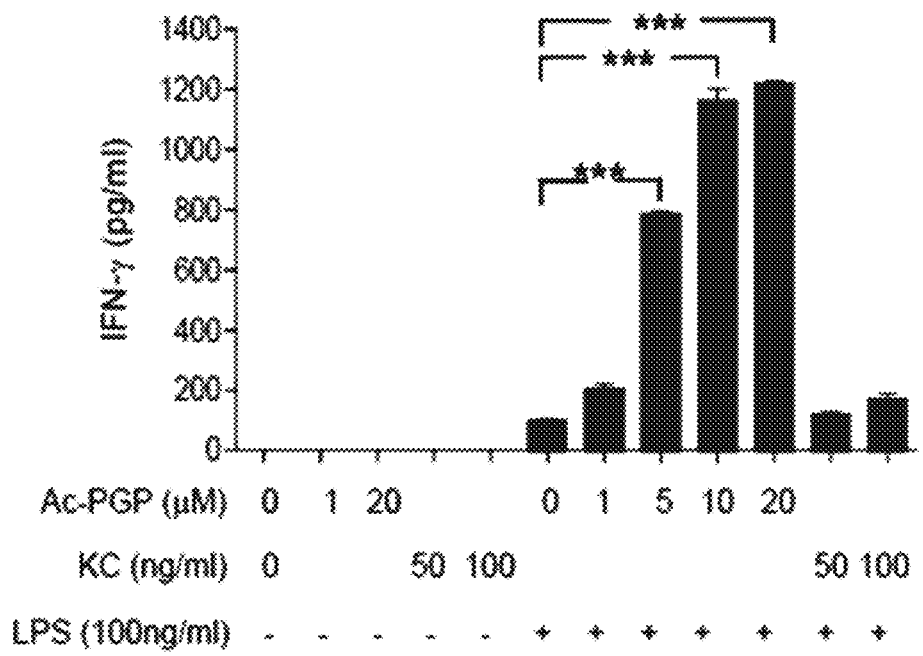
FIG. 24 shows an effect of Ac-PGP on a production amount of IFN-γ in splenocytes of mice stimulated with LPS.
Figure 25:
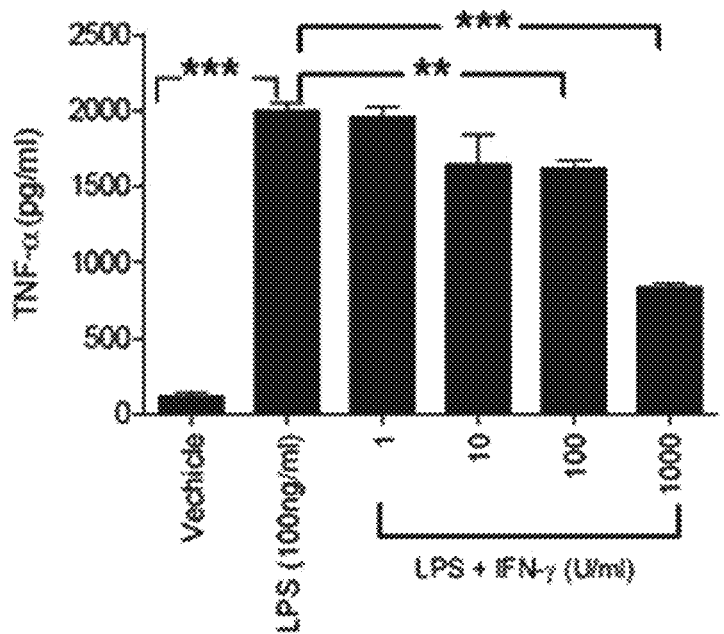
FIG. 25 shows an amount of TNF-α produced in the splenocytes of the mice stimulated with LPS in the presence or absence of IFN-γ.
Figure 26:
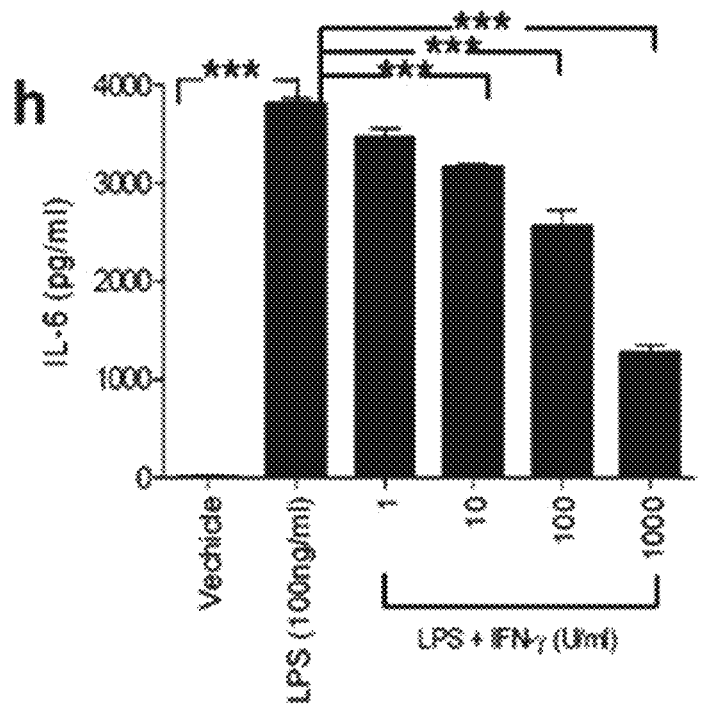
FIG. 26 shows an amount of IL-6 produced in the splenocytes of the mice stimulated with LPS in the presence or absence of IFN-γ.

Since it was confirmed that the administration of the Ac-PGP improved in vivo production of IFN-γ, a direct effect of the Ac-PGP on production of IFN-γ by splenocytes was examined. As shown in FIG. 24, activation of the splenocytes with the Ac-PGP increased production of IFN-γ by LPS. Also, an effect of IFN-γ on production of the pro-inflammatory cytokines was also examined. Stimulation of the mouse splenocytes with IFN-γ relieved production of TNF-α and IL-6 by LPS (FIGS. 25 and 26).

Figure 27:
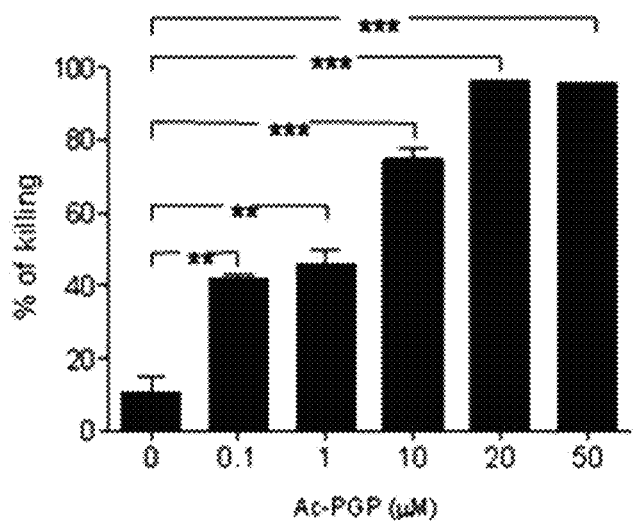
FIG. 27 shows a bacteriocidal effect of Ac-PGP on *E. coli* in neutrophils derived from a human being.
Figure 28:
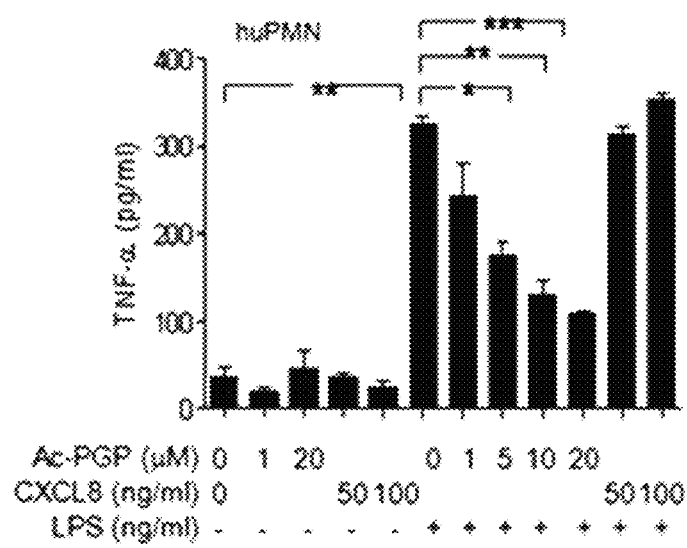
FIG. 28 shows an effect of Ac-PGP or CXCL8 on a production amount of a pro-inflammatory cytokine, TNF-α, in splenocytes from a human being using LPS.
Figure 29:
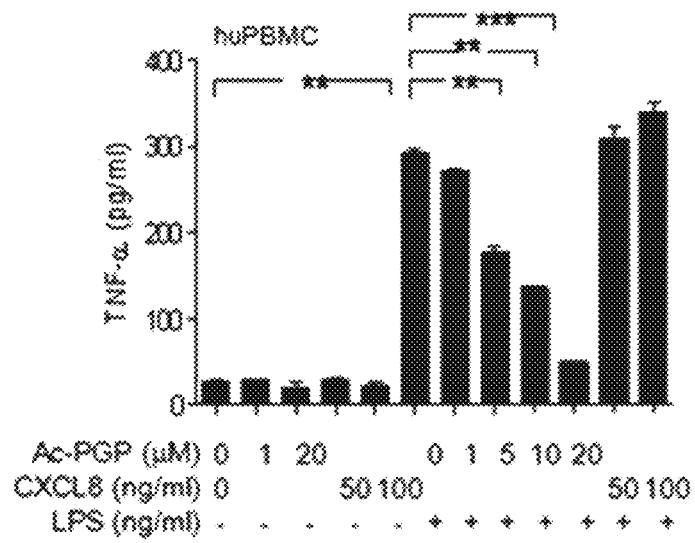
FIG. 29 shows an effect of Ac-PGP or CXCL8 on a production amount of a pro-inflammatory cytokine, TNF-α, in PBMCs from a human being using LPS.

6. Ac-PGP Promotes Bacteriocidal Effect and IFN-γ Production but Suppressing Production of TNF-α in Human Neutrophils and PBMCs Induced by LPS Since Ac-PGP strongly promoted the disinfection activity of the mouse neutrophils, a bacteriocidal effect of the Ac-PGP on human neutrophils was examined. The Ac-PGP exhibited a dose-dependent effect on bacterial killing by the human neutrophils. A extremely small amount (for example, 100 nM) of the Ac-PGP remarkably improved the disinfection activity, and 20 nM of the Ac-PGP almost completely killed opsonified *E. coli* (FIG. 27).

Figure 30:
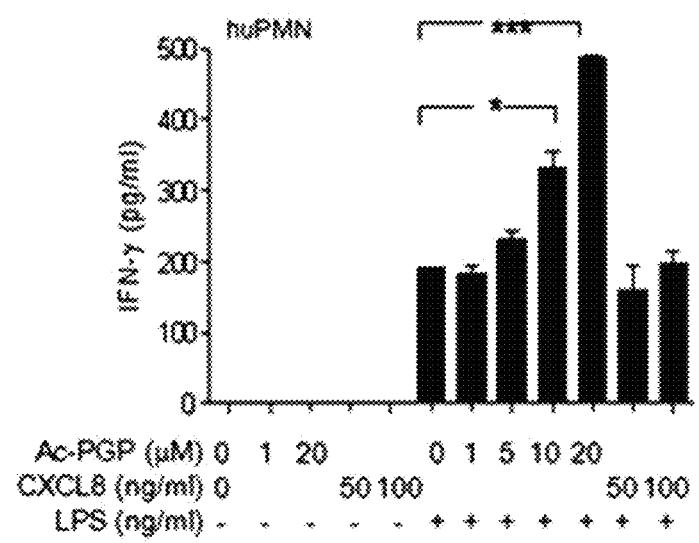
FIG. 30 shows an effect of Ac-PGP on a production amount of IFN-γ in splenocytes derived from a human being stimulated with LPS.
Figure 31:
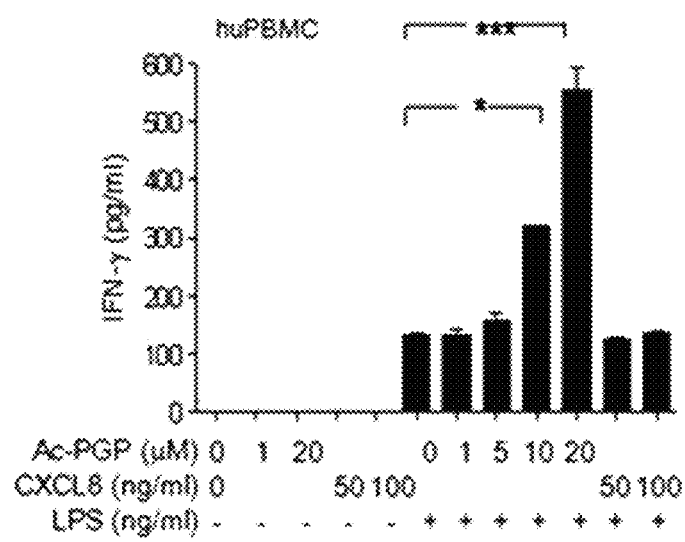
FIG. 31 shows an effect of Ac-PGP on a production amount of IFN-γ in PBMCs derived from a human being stimulated with LPS.

Next, an effect of the Ac-PGP on production of cytokines by human neutrophils and PBMCs was examined. In vitro production of TNF-α by the human being neutrophil or PBMCs stimulated with LPS similarly to the mouse splenocytes was remarkably suppressed by treatment with the Ac-PGP (FIGS. 28 and 29), while production of IFN-γ was remarkably improved by treatment with the Ac-PGP (FIGS. 30 and 31). A human CXCR2 chemokine agonist CXCL8 had few effects on production of TNF-α or IFN-γ stimulated with LPS (FIG. 28 to FIG. 31). Therefore, the Ac-PGP could improve both antiseptic activities in leukocytes derived from human beings and mice.

INDUSTRIAL APPLICABILITY

The pharmaceutical composition for treating an infectious or inflammatory disease according to the present invention can be useful in effectively preventing and treating various infectious or inflammatory diseases including sepsis and septic shock.

A number of examples have been described above. Nevertheless, it will be understood that various modifications may be made. For example, suitable results may be achieved if the described techniques are performed in a different order and/or if components in a described system, architecture, device, or circuit are combined in a different manner and/or replaced or supplemented by other components or their equivalents. Accordingly, other implementations are within the scope of the following claims.

The invention claimed is:

1. A method of using a pharmaceutical composition to treat an inflammatory disease, comprising:
   administering a pharmaceutical composition comprising a peptide ligand that binds with CXCR2 to a subject having an inflammatory disease,
   wherein the inflammatory disease is sepsis or septic shock, and the peptide ligand is acetylated-Pro-Gly-Pro (Ac-PGP).

2. The method of claim 1, wherein the pharmaceutical composition is administered by a subcutaneous injection.

3. The method of claim 1, wherein the pharmaceutical composition is administered at an effective amount of 1 to 200 mg per 1 kg of body weight.

* * * * *